United States Patent
Pace

Patent Number: 5,419,184
Date of Patent: May 30, 1995

[54] HYDROSTATIC PRESSURE TESTING APPARATUS

[76] Inventor: Floyd E. Pace, 1012 Donald Dr., Longview, Tex. 75604

[21] Appl. No.: 127,766

[22] Filed: Sep. 28, 1993

[51] Int. Cl.6 .............................................. G01M 3/28
[52] U.S. Cl. .................................................... 73/49.6
[58] Field of Search ........................ 73/49.6, 49.5, 49.1

[56] References Cited

U.S. PATENT DOCUMENTS

| | | | |
|---|---|---|---|
| 1,851,345 | 3/1932 | Brown et al. | 73/49.6 |
| 2,610,651 | 9/1952 | Hahn. | |
| 3,499,469 | 3/1970 | Vizuete et al. | |
| 3,500,680 | 3/1970 | Ligon et al. | |
| 3,765,560 | 10/1973 | Kemp. | |
| 4,067,228 | 1/1978 | Elle et al. | 73/49.5 X |
| 4,237,936 | 12/1980 | Lossis et al. | 73/49.5 X |
| 4,393,674 | 7/1983 | Rasmussen | 73/49.5 X |
| 4,413,501 | 11/1983 | Schröck | 73/49.6 |
| 4,502,323 | 3/1985 | Watase et al. | 73/49.6 |
| 4,574,618 | 3/1986 | Anthony | 73/40.5 R |
| 4,872,336 | 10/1989 | Baillie | 73/40.5 R |

FOREIGN PATENT DOCUMENTS 546864  3/1932  Germany ................. 73/49.5

*Primary Examiner*—Hezron E. Williams
*Assistant Examiner*—Joseph W. Roskos
*Attorney, Agent, or Firm*—Crutsinger & Booth

[57] ABSTRACT

Hydrostatic pressure testing apparatus for sealing and delivering fluid into a pipe wherein the pipe wall is maintained in tension. A pair of cam actuated movable jaws are mounted on a body for engaging the outer wall of the pipe. A seal ring on a mandrel is positioned to expand into sealing engagement with the inner wall of the pipe. A shaped passage in segments of a split die block lock behind the upset portion on the end of the pipe.

11 Claims, 5 Drawing Sheets

HYDROSTATIC PRESSURE TESTING APPARATUS

TECHNICAL FIELD

A hydrostatic pressure testing apparatus is disclosed for high pressure testing joints of tubing wherein the wall of the tubing is in tension during testing.

BACKGROUND OF INVENTION

Joints of pipe or tubing used in a well are generally connected end to end and suspended vertically in the well such that each joint of pipe is in tension. The types of force which may act on a body are shear or tangential force, tensile force, and compressive force.

Pressure testing devices of the type disclosed in U.S. Pat. No. 4,067,228 for joints of pipe often include heads which are urged into sealing engagement with opposite ends of the joint of pipe to prevent the escape of pressurized water forced into the pipe. The heads are generally urged by hydraulic or mechanical jacks into sealing relation with ends of the joint of pipe, which puts walls of the pipe in compression. When pressurized fluid is delivered into the pipe, stress in the tubing wall is not an accurate reproduction of the stress in the pipe wall when it is pressurized while suspended in a tubing string.

Some pressure testing devices for joints of pipe or tubing require that threaded caps or plugs be attached to threads on opposite ends of the joint. This type of pressure testing device maintains walls of the tubing in tension while the joint is being pressure tested. However, the use of threaded sealing apparatus is undesirable because of the time required for attaching the sealing devices and because the threaded sealing devices may damage threads on the joint of pipe while they are being connected and disconnected from the pipe.

Pressure testing devices have been developed for relatively thin wall tubing which is pressure tested at low pressures. U.S. Pat. No. 2,610,651 discloses a plug assembly for pressure testing pipe which includes a plug member having a threaded end to receive a hub section of a hand wheel. The hand wheel moves the hub section inwardly toward the pipe section such that a follower is pressed against an annular pressure transmitting member which in turn presses against members until they make contact with each other for compressing and forcing seal rings into sealing engagement with the interior wall of the pipe. The pressure to which the pipe can be tested is limited by frictional forces between the seal rings and the walls retaining the plug assemblies in the pipe which will be overcome by the longitudinal component of fluid pressure within the pipe tending to expel the plug assemblies from opposite ends of the pipe. The patent also discloses a second embodiment which incorporates resilient seal rings which are urged into sealing engagement with the outer wall of the pipe.

U.S. Pat. No. 3,765,560 discloses sealing apparatus for pressure testing a pressure vessel which grippingly engages outer walls of a tubular member for holding an expandable seal in position adjacent an inner wall of the pressure vessel. Fluid pressure urges the expandable seal into sealing engagement with inner surfaces of the vessel. Wedge shaped rings, in sliding relation with inclined surfaces on legs secured to the apparatus, apply force to the outer wall of the vessel for holding the pressure testing apparatus in position.

A long felt need exists for hydrostatic pressure testing apparatus which is capable of testing joints of relatively thick walled tubing to a high pressure, for example 2000 pounds per square inch, while the pipe section is in tension to more nearly simulate conditions to which the pipe section will be subjected in the field under normal operating conditions.

SUMMARY OF INVENTION

A pair of sealing heads grippingly engage the outer wall of a joint of pipe or tubing while hydraulic pressure urges a seal ring into sealing engagement with an inner wall of the joint of tubing. Hydraulic pressure inside the tubing urges the heads outwardly and longitudinally of the joint such that the tubing wall is maintained in tension while the joint is being pressure tested.

The method of pressure testing a joint of pipe or tubing generally involves the positioning a joint of pipe between sealing heads having injectors and pipe gripper jaws; moving the sealing heads longitudinally of the joint of pipe to position the injectors and pipe gripper jaws relative to opposite ends of the joint of pipe; moving the pipe gripper jaws for gripping the outer wall of the joint of pipe adjacent opposite ends; moving seals generally radially of the joint of pipe into engagement with the inner wall of the joint of pipe adjacent opposite ends of the joint; pressurizing the inside of the joint of pipe through the injectors; and moving the heads to disengage opposite ends of the joint of pipe. A method preferably includes swing the jaws about generally vertical axes from an open position spaced from the outer wall of the joint of pipe to a closed position engaging the outer wall of the joint of pipe. Force tending to eject the seal from inside the joint of pipe is transferred through the sealing head to the gripper jaws engaging the outer wall of the joint of pipe. Thus, the wall of the joint of pipe is in tension while it is being tested.

A preferred embodiment of the sealing head for sealing pipe having a wall with inner and outer wall surfaces includes a box section having an entrance opening; an injector in the box section for delivering pressurized fluid into a pipe extending through the entrance opening; and a die block assembly in the box section formed of a pair of die block segments. The die block assembly preferably includes a split die block formed of die block segments having a passage generally conforming to the shape of the outer wall of the pipe.

Preferably, a pair of cam actuators move at least one of the die block segments into engagement with the end of the pipe such that the wall of the pipe is in tension during testing. Since the inside and outside diameters of the pipe may change as pressure in the pipe increases, the actuators preferably accommodate these changes without crushing or disengaging the pipe. However, other actuators may replace the cam actuators without departing from the general concept of the invention.

A primary object of the invention is to provide a pipe testing device capable of maintaining walls of a joint of pipe in tension while the joint is subjected to several thousand pounds of internal pressure.

Another object is to provide a method and apparatus for removably mounting die blocks on arms which are actuated for gripping the end of the pipe joint, in combination with nozzles which seal against the inside wall of the pipe and deliver pressurized fluid. The die blocks can be replaced to accommodate joints of different outside diameters to prevent scoring or otherwise damaging the joint of pipe.

DESCRIPTION OF DRAWINGS

Drawings of a preferred embodiment of the invention are annexed hereto so that the invention may be better and more fully understood, in which.

Numeral references are employed to designate like parts throughout the various figures of the drawing.

DESCRIPTION OF A PREFERRED EMBODIMENT

Figure 1:
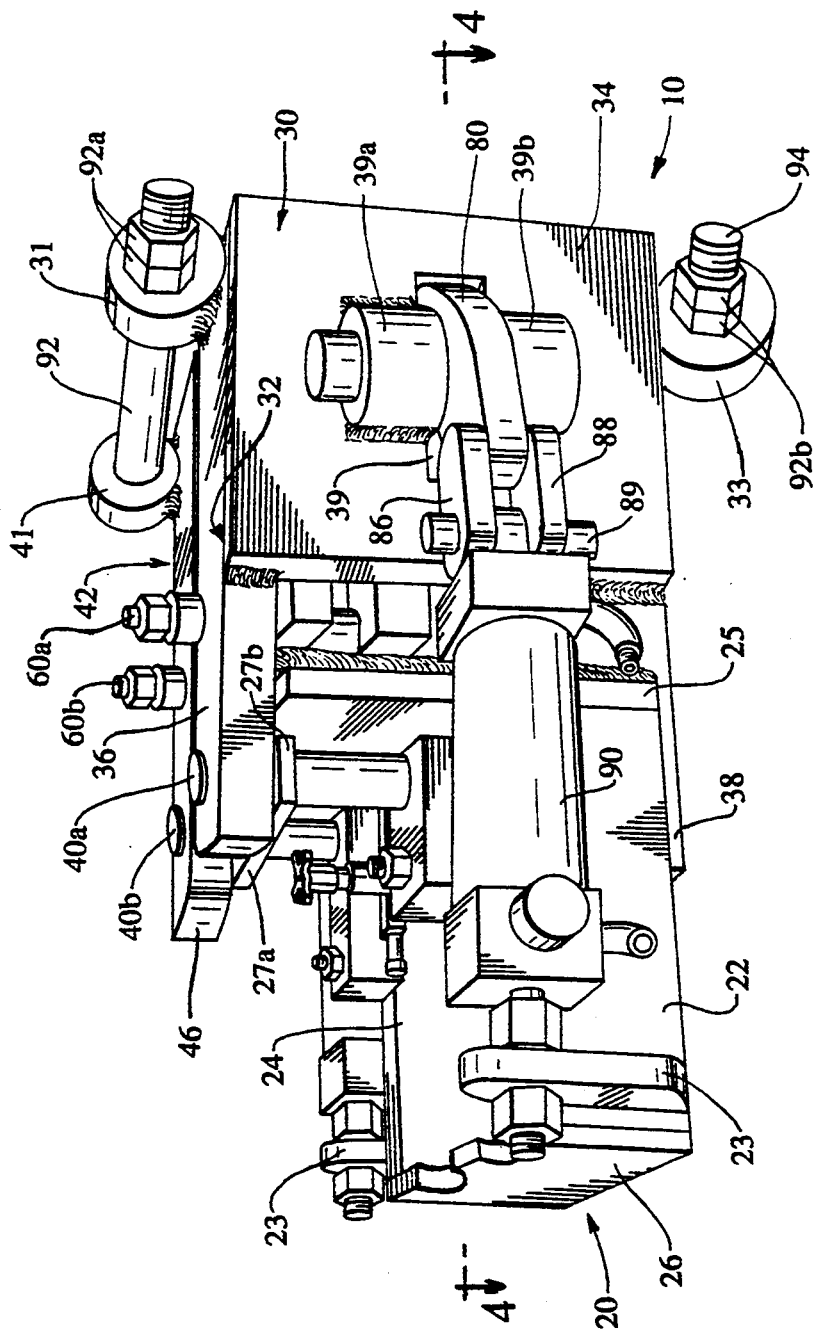
FIG. 1 is a perspective view illustrating the hydrostatic pressure testing apparatus.

Referring to FIG. 1 of the drawing, the numeral 10 generally designates a head for sealing against the end of a joint of pipe and injecting water or other pressurized fluid into the inside of the pipe for pressure testing the pipe. It should be appreciated that a head will be used at each end of the joint of pipe.

Figure 4:
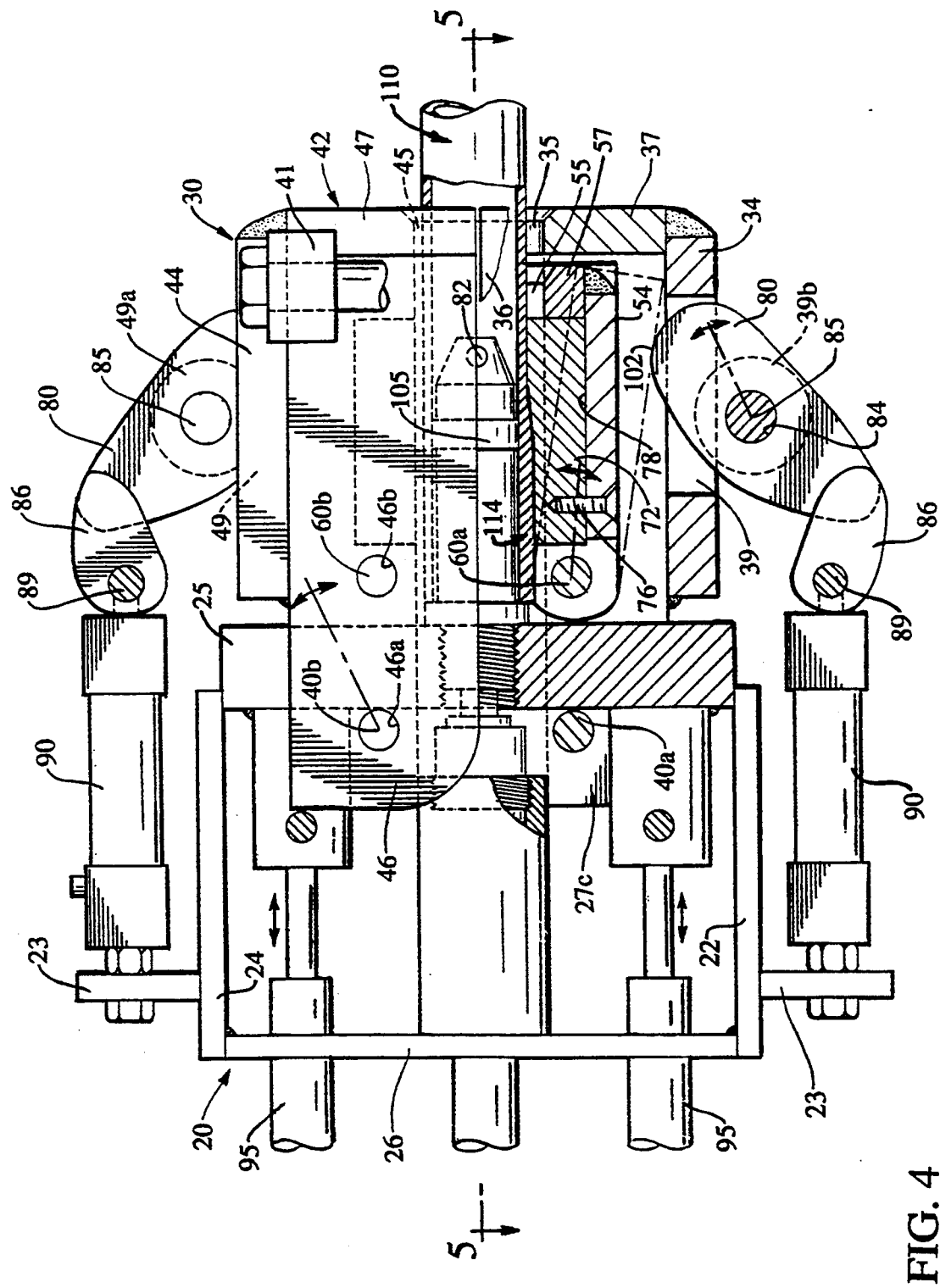
FIG. 4 is a cross-sectional view taken along line 4—4 of FIG. 1.
Figure 5:
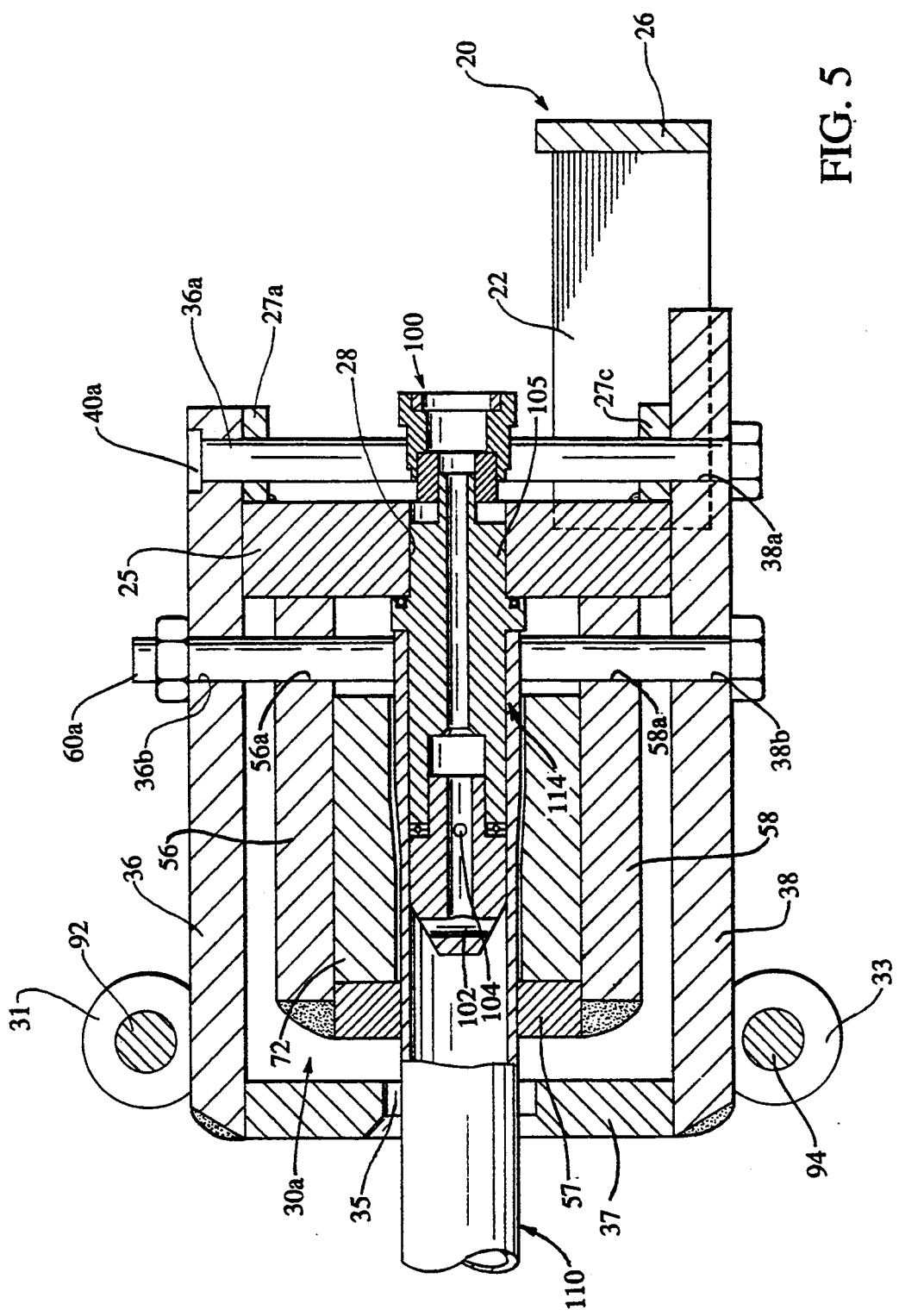
FIG. 5 is a cross-sectional view taken along line 5—5 of FIG. 4.

Referring to FIGS. 1, 4 and 5 of the drawing, sealing head 10 includes a carriage 20 formed by a pair of spaced side walls 22 and 24 having a front mounting plate 25 and a rear wall 26 welded or otherwise secured to opposite ends of side walls 22 and 24. A pair of mounting ears 23 are welded or otherwise secured to side walls 22 and 24 of carriage 20.

Lugs 27A and 27B are welded or otherwise secured adjacent the upper edge of front mounting wall 25 and a base plate 27C is welded or otherwise secured adjacent the lower edge of front mounting plate 25. Each of the lugs 27A and 27B has a bolt receiving passage formed therethrough and base plate 27C has bolt receiving passages extending therethrough vertically below the bolt receiving passages formed in lugs 27A and 27B.

Terms such as "left," "right," "clockwise," "counterclockwise, . . . horizontal," "vertical," "up," and "down" when used in reference to the drawings, generally refer to orientation of the parts in the illustrated embodiment and not necessarily during use. These terms used herein are meant only to refer to relative positions and/or orientations, for convenience, and are not to be understood to be in any manner otherwise limiting.

As best illustrated in FIGS. 4 and 5 of the drawing, the elements of carriage 20 form a strong rigid generally rectangular frame for carrying other components of the sealing head 10.

Figures 2, 3:
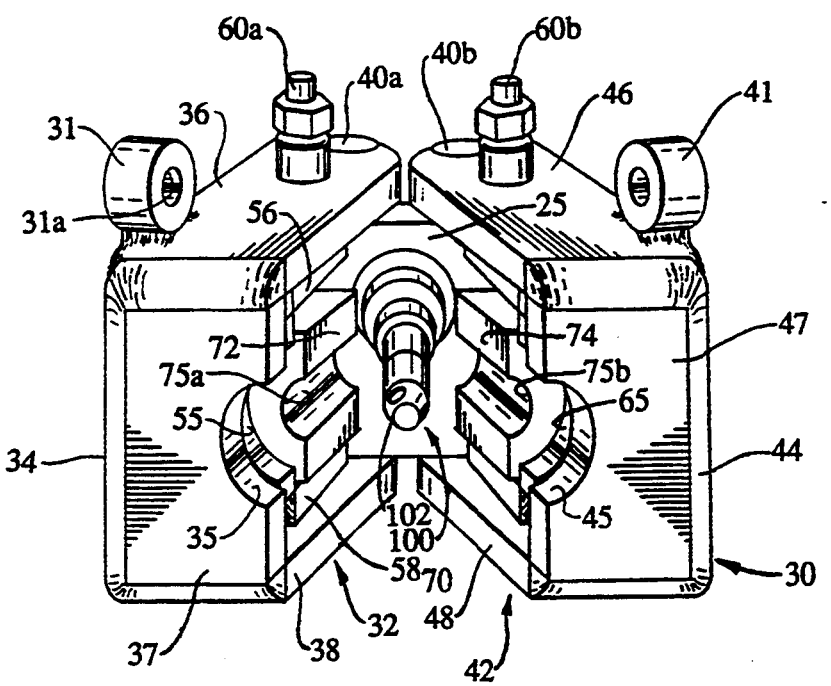
FIG. 2 is a front elevational view illustrating the pressure testing apparatus in an open position.
FIG. 3 is a front elevational view similar to FIG. 2, movable jaws being illustrated in position to grip the end of a joint of pipe.

Sealing head 10 includes a box section, generally designated by the numeral 30 in FIGS. 2, 3 and 5 of the drawing. Box section 30 is formed by a pair of box segments 32 and 42 to provide a chamber 30A.

Box segment 32 is formed by a vertically extending side wall 34 having top and bottom arms 36 and 38 mounted adjacent upper and lower edges thereof. A face plate 37 has one edge welded to side wall 34 and upper and lower edges welded to outer ends of top arm 36 and bottom arm 38. Face plate 37 has a semicircular passage 35 formed in its other edge.

As best illustrated in FIG. 1 of the drawing, a boss 31 is welded or otherwise secured to top arm 36 and a boss 33 is welded or otherwise secured to bottom arm 38. Bosses 31 and 33 have passages extending therethrough for receiving a tie bolt, as will hereinafter be more fully explained.

Top arm 36 and bottom arm 38 have holes 36A and 38A, respectively, formed adjacent rear ends thereof for receiving mounting pins, as will hereinafter be more fully explained. Top arm 36 and bottom arm 38 also have holes 36B and 38B formed in a central section thereof for receiving mounting bolts, as will hereinafter be more fully explained.

As best illustrated in FIGS. 1 and 4 of the drawing, side wall 34 of box segment 32 has a slot 39 formed therein and a pair of sleeves 39A and 39B secured to side wall 34 adjacent upper and lower edges of slot 39.

Box segment 42 is substantially identical to box section 32 except that box segment 42 is a mirror image of box segment 32.

Box segment 42 is formed by a vertically extending side wall 44 having top and bottom arms 46 and 48 mounted adjacent upper and lower edges thereof. A face plate 47 has one edge welded to side wall 44 and upper and lower edges welded to outer ends of top arm 46 and bottom arm 48. Face plate 47 has a semicircular passage 45 formed in its other edge.

As best illustrated in FIG. 1 of the drawing, a boss 41 is welded or otherwise secured to top arm 46 and a boss 43 is welded or otherwise secured to bottom arm 48. Bosses 41 and 43 have passages extending therethrough for receiving tie bolts 92 and 94, as will hereinafter be more fully explained.

Top arm 46 and bottom arm 48 have holes 46A and 48A, respectively, formed adjacent rear ends thereof for receiving mounting pins, as will hereinafter be more fully explained. Top arm 46 and bottom arm 48 also have holes 46A and 48B formed in a central section thereof for receiving mounting bolts, as will hereinafter be more fully explained.

As best illustrated in FIG. 4 of the drawing, side wall 44 of box segment 42 has a slot 49 formed therein and a pair of sleeves 49A and 49B secured to side wall 44 adjacent upper and lower edges of slot 49.

As best illustrated in FIG. 5 of the drawing, top arms 36 and 46 extend above upper and lower edges of front mounting plate 25 such that holes 36A and 46A are aligned with holes formed in lugs 27A and 27B and holes 38A and 48A are aligned with the holes formed in base plate 27C. Pivot pin 40A extends through hole 36A, the hole formed in lug 27A, the hole formed in the base plate 27C and through the hole 38A formed in bottom arm 38. Pivot pin 40B extends through hole 46A in top arm 46 and through holes formed in lug 27B and base plate 27C into the hole 48A in bottom arm 48. Thus, box segments 32 and 42 are pivotally secured to carriage 20 for pivotal movement about vertical axes of pivot pins 40A and 40B. Rear surfaces of arms 36, 38, 46 and 48 are shaped such that each arm can swing freely through an angle of at least 90° to provide access to the chamber 30A inside box section 30.

A die block assembly 50 is formed of a pair of die block segments 52 and 62 which carry a split die block 70, as illustrated in FIGS. 2 and 3.

Referring to FIGS. 2, 3, 4 and 5, die block segment 52 is formed by a side wall 54, a top arm 56, a bottom arm 58 and a face plate 57 having a semicircular passage 55 formed therein. Upper and lower arms 56 and 58 have holes 56A and 58A, respectively, formed in rear end portions thereof. Die block segment 52 is pivotally secured by a pivot pin 60A which extends through holes 36B and 38B formed in top and bottom arms 36 and 38 of box segment 32. Pivot pin 60A extends through holes 56A and 58A in top and bottom arms 56 and 58, respectively, of die block segment 52.

Die block segment 62 is formed by a side wall 64, a top arm 66, a bottom arm 68 and a face plate 67 having a semicircular passage 65 formed therein. Upper and lower arms 66 and 68 have holes 66A and 68A, respectively, formed in rear end portions thereof. Die block segment 62 is pivotally secured by a pivot pin 60B which extends through holes 36B and 38B formed in top and bottom arms 36 and 38 of box segment 32. Pivot pin 60B extends through holes 66A and 68A in top and bottom arms 66 and 68, respectively, of die block segment 62.

Opposite ends of joints of tubing having upset ends vary in dimensions of the inside and outside diameter of the tubing. For example, a 32 foot joint of 2⅜" O.D. tubing has an inside diameter of approximately 1.995 inches. The outside diameter of the upset end of the tubing is 2.594 inches plus or minus 0.0625 inches. The distance from the end of the pipe to the end of the fadeaway is about 6 inches.

Segments 72 and 74 of the split die block preferably have a length of approximately 6 inches.

As illustrated in FIG. 5 of the drawing, the end of the joint of pipe extends, for example, 2 inches past the rear edge of die block 72 such that the upset portion on the end of the joint of pipe is captured in the shaped passage 75 in die block segments 72 and 74. It should be noted that segments 72 and 74 of the die block do not apply substantial compressive force to the walls of the joint of tubing. Further, segments 72 and 74 of split die block 70 are configured to prevent scratching, scoring or otherwise marring the outer surface of the joint of pipe. Any defect in the outer wall of the pipe joint is a possible source of deterioration resulting from exposure of the surface of the pipe to acid, moisture and other elements as well as abrasive surfaces.

A split die block 70 is formed by sections 72 and 74 having a shaped passage 75 formed by substantially semi-cylindrical wall segments 75A and 75B. Wall segments 75A and 75B are preferably machined to substantially match the contour of the outer wall of the end section of the pipe joint. Sections 72 and 74 of split die block 70 are removably secured in seats 78 in die block segments 52 and 62 by set screws 76. For testing pipe of different outside diameters, sections 72 and 74 of split die block 70 may be removed and split die block sections having a passage formed to accommodate the particular size and configuration of pipe to be tested can be installed.

As best illustrated in FIGS. 1 and 4 of the drawing, a cam 80 having pair of rearwardly projecting ears 86 and 88 has a cam face 82 which engages the side wall 54 of die block segment 52. Cam 80 has a central opening 84 for receiving a pivot pin 85 extending through openings in sleeves 39A and 39B when cam face 82 is positioned through slot 39 in side wall 34 of box segment 32. Ears 86 and 88 are spaced apart, as best illustrated in FIG. 1 of the drawing and have openings extending therethrough in which a pivot pin 89 is mounted for securing the piston rod of a pressure-actuated cylinder 90 to cam 80. The base of pressure-actuated cylinder 90 is connected to the mounting ear 23 on carriage 20.

A second cam 80 is mounted on box segment 42 and extends through a slot 49 formed in side wall 44 for engaging the side wall 64 of die block segment 62.

After sections 72 and 74 of split die block 70 have been installed, box segments 32 and 42 are rotated to the position illustrated in FIGS. 1 and 4 of the drawing and tie bolts 92 and 94 are positioned through bosses 31 and 34 and secured in position by lock nuts 92A and 92B.

For pressure testing a joint of pipe, the joint of pipe is moved longitudinally until its end is moved through the opening formed by semicircular passages 35 and 45 in face plates 37 and 47 and through the opening formed by semicircular passages 55 and 65 formed in face plates 57 and 67 on die block segments 52 and 62. When the end of the pipe is in position, cylinders 90 are actuated for rotating cams 80 such that each cam face 82 engages the outer surface of side walls 54 and 64 for moving sections 72 and 74 of the split die block 70 into engagement with the outer wall of the end section of the joint of pipe. Valves are then opened to deliver pressurized fluid through the injectors to the inside of the pipe. It should be readily apparent that sections 72 and 74 of the split die block are firmly held in position to grip the outer surface of the joint of pipe so that no longitudinal force which would apply compressive loading to the joint of pipe is required.

The sealing head 10 is formed by two box segments 32 and 42 each having an interior chamber 30A. Referring to FIG. 5 of the drawing, a pair of tie bolts 92 and 94 extend through eyes on tie box segments 32 and 42 for holding the box segments together. Bolts 92 and 94 can be removed and box segments 32 and 42 swing to provide access to die block segments 52 and 62 in chamber 30A.

Hinge pins 60A and 60B extend through openings in the top and bottom arms of each outer box segment 32 and 42. Split die block sections 72 and 74, each having a semi-circular passage formed therein which mates with the upset end portion on the end of a joint of pipe.

Cam actuators 80 are pivotally connected by a pin 85 to box segments 32 and 34 and engage die block when cam actuating cylinders 90 are actuated.

A pair of rams 95 are mounted to a frame (not shown). When rams 95 are extended the piston rods move carriage 20 mounted on axles toward the end of a pipe. The end on the joint of pipe extends through an entrance opening formed in the face plates of box segments 32 and 34. When the pipe is seated in position, cylinders 90 are actuated thereby rotating cams 80 about cam pins 85 for moving ends 82 of the cams into engagement with die blocks 52 and 62 which carry die segments 72 and 74 and move the die segments into gripping engagement with the end of the pipe.

An injection nozzle 100 having ports 102 formed in side walls thereof delivers water or other pressurized fluid into the pipe joint. Pressure is delivered through ports 104 to engage expandable seal elements 105 which are urged outwardly by water pressure into sealing engagement with the inner wall of pipe joint. After a predetermined pressure has been established in the pipe joint and held for a predetermined period of time, for example, 20,000 p.s.i. held for five seconds, pressure is released and the sealing head is retracted and pulled off of the end of the joint of pipe.

The present apparatus engages the outer wall of the pipe and delivers pressure to the inside of the pipe such that the wall of the pipe is in tension during the testing procedure. However, it is not necessary that the threaded end of the pipe be engaged.

Figure 6:
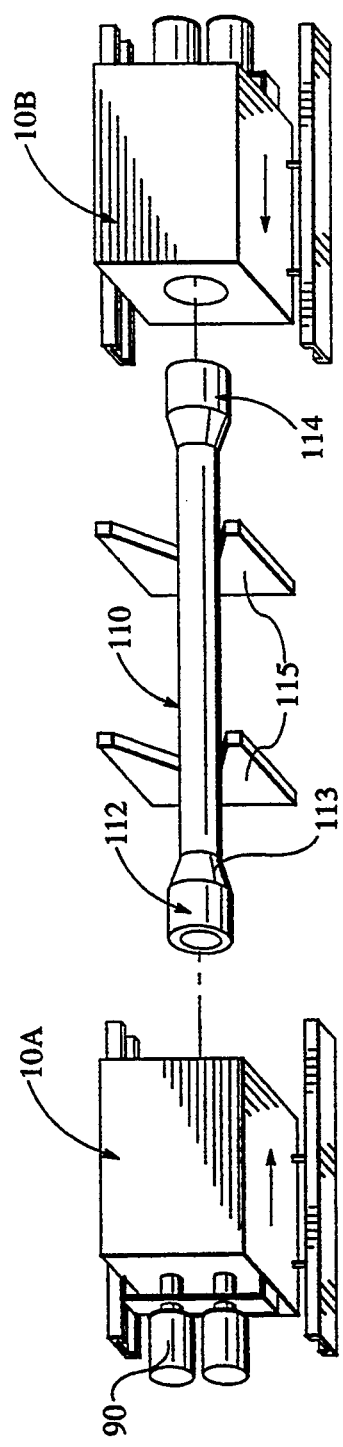
FIG. 6 is a diagrammatic perspective view of a pair of sealing heads positioned adjacent opposite ends of a joint of pipe.

Referring to FIG. 6 of the drawing, a joint 110 of pipe having upset ends 112 and 114 is moved onto cradles 115 configured for aligning the axis of the joint 110 of pipe with a central axis through the mandril 105 of injector 100. Rams 90 are connected through flow dividers for moving heads 10A and 10B such that opposite ends 112 and 114 of the joint 110 of tubing is positioned through the entrance openings in heads 10A and 10B. When opposite ends 112 and 114 are positioned as illustrated in FIG. 5 of the drawings, cylinders 90 are actuated cams 80 such that faces 82 move die block segments 52 and 62 inwardly until the upset end portions 112 and 114 are captured in the shaped passage 75 in segments 72 and 74 of the split die block 70. It should be appreciated that hydraulic force in the joint 110 of pipe is distributed over the fade-away portion 113 of the upset ends 112 and 114.

For use of the pipe testing device on pipe which does not have upset ends, it is contemplated that a relatively soft material having a high coefficient of sliding friction be applied to the inner walls 72A and 74A of the shaped passage 75 in segments 72 and 74 of split die block 70.

It is to be understood that while detailed descriptions of a preferred embodiment has been illustrated and described, the invention is not to be limited to the specific arrangement of parts and specific features herein described and illustrated in the drawing. Rather, the descriptions are merely of an exemplary embodiment of the invention, which may be embodied in various forms.

It should appreciated that other and further embodiments of the invention may be devised without departing from the spirit and scope of the appended claims.

Having described the invention, I claim:

1. A method of pressure testing a joint of pipe having inner and outer walls comprising the steps of:
   positioning a joint of pipe between sealing heads having injectors and pipe engaging jaws;
   moving the sealing heads longitudinally of the joint of pipe to position the injectors and pipe engaging jaws relative to opposite ends of the joint of pipe;
   moving a pair of cams for urging the pipe engaging jaws for engaging the outer wall of the joint of pipe adjacent opposite ends:
   moving seals generally radially of the joint of pipe into engagement with the inner wall of the joint of pipe adjacent opposite ends of the joint;
   pressurizing the inside of the joint of pipe through at least one of the injectors; and
   supporting the sealing heads such that the wall of the joint of pipe is maintained in tension while the inside of the joint of pipe is pressurized.

2. A method of pressure testing a joint of pipe having inner and outer walls according to claim 1, the step of:
   moving a pair of cams for urging the pipe engaging jaws for engaging the outer wall of the joint of pipe adjacent opposite ends comprising the steps of:
   rotating the pair of cams about a first pair of generally vertical axes to apply force for swinging the jaws about a second pair of generally vertical axes from an open position spaced from the outer wall of the joint of pipe to a closed position engaging the outer wall of the joint of pipe.

3. Apparatus for sealing pipe having a wall with inner and outer wall surfaces comprising:
   a box section having an entrance opening;
   an injector in said box section for delivering pressurized fluid into a pipe extending through said entrance opening;
   a die block assembly in said box section said die block assembly being formed by a pair of die block segments;
   a split die block in said die block assembly, said split die block being formed of die block sections having a passage generally conforming to the shape of the outer wall of the pipe; and
   a cam actuator for moving at least one of said die block segments into engagement with the end of the pipe such that the wall of the pipe is in tension during testing.

4. Apparatus for sealing pipe having a wall with inner and outer wall surfaces, according to claim 3, said box section comprising:
   a pair of box segments movably secured together.

5. Apparatus for sealing pipe having a wall with inner and outer wall surfaces, according to claim 3, said injector comprising:
   an injector body; and
   a seal on said body positioned to move into sealing engagement with the surface of the pipe wall.

6. Apparatus for sealing pipe according to claim 3 said die block assembly comprising;
   a plurality of jaws, at least one of said jaws being movable to engage and disengage the pipe wall.

7. Apparatus for sealing pipe according to claim 6 with the addition of:
   an actuator secured between said box section and said movable jaw for moving said movable jaw relative to said box section.

8. Apparatus for sealing pipe according to claim 3, said seal comprising:
   a mandrel having a groove and a passage communicating with said groove;
   and a seal ring in said groove, said seal ring being urged by fluid pressure into engagement with the pipe wall.

9. Apparatus for sealing pipe according to claim 3, said cam actuator comprising:
   a cam movably secured to said box section and having a surface that moves said movable jaw relative to said box section.

10. Apparatus for sealing pipe having a wall with inner and outer wall surfaces, said outer wall surfaces having upset end portions, comprising:
    a pair of sealing heads;
    a pair of die block sections on each of said sealing heads, each die block section having a shaped passage to substantially match the contour of the upset end portion of the outer wall of the pipe;
    actuator means for moving and maintaining at least one of said die block sections into engagement with the upset end portion of the pipe for limiting movement of said seal head longitudinally relative to the pipe; and
    means on said seal head for sealingly engaging the inner wall of the pipe and delivering pressurized fluid into the pipe such that walls of the pipe are maintained in tension while the inside of the pipe is pressurized.

11. Apparatus for sealing pipe according to claim 10 with the addition of means mounting said die block sections for removal to permit mounting of different die block sections having a passage formed to accommodate particular sizes and configurations of upset end portions of different configurations of pipe to be tested.

* * * * *